United States Patent
Mayer et al.

(10) Patent No.: US 7,501,384 B2
(45) Date of Patent: Mar. 10, 2009

(54) CRYSTALLINE MODIFICATION OF THE ANHYDRATE OF BOSCALID

(75) Inventors: Winfried Mayer, Bubenheim (DE); Hans Ziegler, Mutterstadt (DE); Karl-Heinrich Schneider, Kleinkarlbach (DE); Thomas Kröhl, Mainz (DE); Horst Mayer, Ludwigshafen (DE); Peter Erk, Frankenthal (DE); Gerhard Cox, Bad Dürkheim (DE); Reinhard Stierl, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 493 days.

(21) Appl. No.: 10/544,627

(22) PCT Filed: Jan. 28, 2004

(86) PCT No.: PCT/EP2004/000703

§ 371 (c)(1), (2), (4) Date: Aug. 5, 2005

(87) PCT Pub. No.: WO2004/072039

PCT Pub. Date: Aug. 26, 2004

(65) Prior Publication Data

US 2006/0154825 A1    Jul. 13, 2006

(30) Foreign Application Priority Data

Feb. 14, 2003 (DE) ................................ 103 07 751

(51) Int. Cl.
*C07D 213/56* (2006.01)
*A01N 43/40* (2006.01)
(52) U.S. Cl. ...................... 504/244; 546/316
(58) Field of Classification Search .............. None
See application file for complete search history.

(56) References Cited

U.S. PATENT DOCUMENTS

| 5,330,995 A | 7/1994 | Eicken et al. |
| 5,480,897 A | 1/1996 | Eicken et al. |
| 5,556,988 A | 9/1996 | Eicken et al. |
| 5,589,493 A | 12/1996 | Eicken et al. |
| 6,350,765 B1 | 2/2002 | Schelberger et al. |

FOREIGN PATENT DOCUMENTS

| EP | 0 210 320 B1 | 5/1989 |
| EP | 0 545 099 A | 6/1993 |
| WO | WO-99/31979 A | 7/1999 |
| WO | WO-03/029219 A | 4/2003 |
| WO | WO-03/090538 A1 | 11/2003 |

OTHER PUBLICATIONS

Derwent publication No. 2003-354720/33, Abtract of WO 03/029219, BADI Sep. 25, 2001.
Derwent publication No. 2003-854345/79, Abstract of WO-A1-03/090538, BADI Mar. 21, 2002.

*Primary Examiner*—Zinna N Davis
(74) *Attorney, Agent, or Firm*—Birch, Stewart, Kolasch & Birch, LLP

(57) ABSTRACT

Monoclinic 2-chloro-N-(4'-chlorobiphenyl-2-yl)nicotinamide melting at 147-148° C. and of the formula I

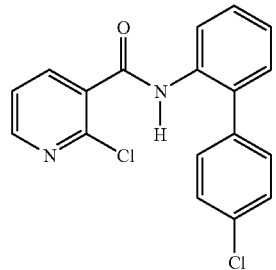

and a process for the preparation thereof.

11 Claims, No Drawings

CRYSTALLINE MODIFICATION OF THE ANHYDRATE OF BOSCALID

This application is a 371 of PCT/EP04/00703 filed Jan. 28, 2004.

The present invention relates to monoclinic 2-chloro-N-(4'-chlorobiphenyl-2-yl)-nicotinamide melting at 147-148° C. and of the formula I

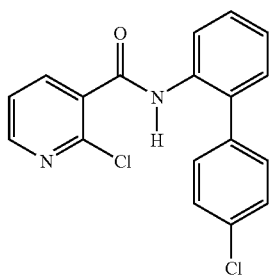

The present invention furthermore relates to the preparation thereof:

Monoclinic 2-chloro-N-(4'-chlorobiphenyl-2-yl)nicotinamide melting at 144-145° C. and of the formula I is described in EP-A-545 099 and PCT/EP02/10320 and is known under the common name boscalid. PCT/EP02/10320 describes the anhydrate and the hydrate of boscalid and also the preparation of boscalid hydrate from boscalid anhydrate.

The known anhydrate of boscalid is referred to in this Application as modification I and the anhydrate of boscalid as claimed in claim 1 is referred to as modification II.

In order to prepare an aqueous suspension concentrate (SC) or a suspoemulsion (SE) from the anhydrate of boscalid, according to PCT/EP02/10320 it is first necessary to prepare the hydrate of boscalid, which is then very finely milled in the presence of water and further assistants. This is not possible with the anhydrate of boscalid since, when this is milled with the assistants in water, it forms a loamy solid which hinders the further milling process.

According to PCT/EP02/10320, the hydrate of boscalid of modification I is prepared by dissolving the anhydrate of boscalid of modification I in a water-soluble solvent and then precipitating the hydrate by adding water.

Solid formulations, such as spray-dried or extruded water-dispersible granules, can be prepared directly from the anhydrate of boscalid of modification I without having to carry out a conversion to the hydrate beforehand.

If these water-dispersible granules are then diluted with water and are mixed with solvent-containing crop protection preparations, for example emulsion concentrates (EC), problems may arise during application since boscalid crystals form and may then block the filters in application apparatuses.

It is an object of the present invention to eliminate the deficiencies described in the case of the water-dispersible granules.

We have found that this object is achieved by providing the monoclinic anhydrate of boscalid of the formula I of modification II which melts at 147-148° C. Surprisingly, it was found that the anhydrate of boscalid of the formula I in the form of modification II shows scarcely any crystal growth in the presence of solvents.

The preparation of the anhydrate of boscalid of formula I of modification I is described in EP-A-545 099 and PCT/EP02/10320.

The present invention furthermore relates to processes for the preparation of anhydrate of boscalid of modification II.

In one embodiment (process 1), the process comprises the following steps:
a) dissolution of the anhydrate of the compound of the formula I of modification I in a polar organic solvent or an aromatic hydrocarbon,
b) precipitation of the anhydrate of the compound of the formula I of modification II by cooling the solvent.

Suitable polar solvents are alcohols, glycols, ketones, ethers, esters, amides and mixtures of these solvents. Aromatic hydrocarbons are furthermore suitable.

Examples of alcohols are methanol, ethanol and propanol. Methanol is particularly preferred.

Suitable glycols are, for example, ethylene glycol and diethylene glycol.

Suitable ketones are, for example, acetone and cyclohexanone.

Suitable ethers are, for example, dioxane and tetrahydrofuran.

A suitable ester is, for example, ethyl acetate.

A suitable amide is, for example, dimethylformamide.

Suitable aromatic solvents are, for example, benzene, toluene and xylene.

The dissolution of the anhydrate of the compound of the formula I of modification I in stage a) is effected at from 20 to 150° C., preferably from 40 to 115° C., particularly preferably from 50 to 95° C.

The precipitation of the anhydrate of the compound of the formula I of modification II in stage b) is effected by cooling the solution obtained in stage a) to temperatures of from 0 to 30° C., preferably from 10 to 25° C., particularly preferably from 20 to 25° C. The precipitation is effected over a period of from 1 to 24, preferably from 2 to 20, hours.

The addition of seed crystals of the anhydrate of the compound of the formula I of modification II in stage b) is particularly advantageous, substantially accelerating the precipitation.

In a further embodiment of (process 2), the process comprises the following steps:
a) heating of the anhydrate of the compound of the formula I of modification I to above 150° C. until everything has melted,
b) cooling of the melt with addition of seed crystals of the anhydrate of the compound of the formula I of modification II.

The seed crystals are added in stage b) in an amount of from 0.01 to 20, preferably from 0.5 to 5, % by weight.

This process is preferably carried out in a suitable stainless steel vessel. The conversion of the anhydrate of the compound of the formula I of modification I into modification II takes place quantitatively.

The physical properties of the two modifications of the anhydrates of the compound of the formula I are compared in table 1:

TABLE 1

| Properties | Anhydrate, modification I | Anhydrate, modification II |
|---|---|---|
| Molecular weight [g/mol] | 342 | 342 |
| Melting point [° C.] (DSC) | 144.8 | 147.2 |
| Heat of fusion [J/g] (DSC) | 85 | 106 |

TABLE 1-continued

| Properties | Anhydrate, modification I | Anhydrate, modification II |
|---|---|---|
| Density [g/cm$^3$] | 1.399 | 1.457 |
| Characteristic IR bands [cm$^{-1}$] | 924, 1310, 1650 | 868, 917, 1675 |

The cell parameters from the crystallographic investigations using a single crystal diffractometer from Siemens are shown in table 2:

TABLE 2

| Parameter | Anhydrate, modification I | Anhydrate, modification II |
|---|---|---|
| Class | Monoclinic | Monoclinic |
| Space group | P21/c | P21/c |
| a | 1479.2(3) pm | 1162.5(6) pm |
| b | 1157.67(19) pm | 1134.2(4) pm |
| c | 1872.1(3) pm | 1283.2(5) pm |
| α | 90° | 90° |
| β | 91.993(17)° | 114.52(4)° |
| γ | 90° | 90° |
| Volume | 3.2038(9) nm$^3$ | 1.5390 nm$^3$ |
| Z | 8 | 4 |
| Density (calculated) | 1.423 mg/m$^3$ | 1.481 mg/m$^3$ |
| R$^1$, wR$^2$ | 0.1036; 0.1699 | 0.0489; 0.1264 |

The parameters shown have the following meaning:
a, b, c = edge lengths of the unit cell
α, β, γ = corresponding angles
Z = number of molecules in the unit cell

EXAMPLE 1

Preparation of the Anhydrate of the Compound of the Formula I of Modification II:

30 g of methanol are initially taken in a conical flask having a ground glass joint. Thereafter, 5 g of anhydrate of the compound of the formula I of modification I are added and the mixture is heated to 55° C. in a water bath while stirring until everything has dissolved (about 10 minutes). Thereafter, the flask is removed from the heating bath and then left to cool for a period of 18 hours at ambient temperature (about 20° C.). Anhydrate of the compound of the formula I of modification II crystallizes out. Melting point 147.2° C.

EXAMPLE 2

200 g of anhydrate of the compound of the formula I of modification I are heated to 160° C. in a stainless steel vessel. The melt is then cooled while stirring. At 150° C., seeding is effected with crystals of the anhydrate of the compound of the formula I of modification II and cooling is continued. Anhydrate of the compound of the formula I of modification II is obtained.

EXAMPLE 3

Preparation of Water-dispersible Granules of Anhydrate of the Compound of the Formula I of Modification I or II:

Composition:

| Component | Concentration |
|---|---|
| Boscalid (active ingredient) | 30-60% w/w |
| Dispersant (ligninsulfonate salt) | 10-20% w/w |
| Wetting agent (naphthalenesulfonic acid condensate salt) | 5-10% w/w |
| Antifoam (silicone oil) | 0.5-1% w/w |
| Standardizing agent (sodium sulfate) | to 100% |

Preparation Process:

A suspension of suitable concentration is prepared and is milled to the desired particle size (50%<2 μm) by means of a pearl mill. The suspension is then dried in a spray tower.

Comparison of the Tank Mixing Compatibility:

For this purpose, both water-dispersible granules of the above composition, comprising anhydrate of the compound of the formula I of modification I (formulation A), and water-dispersible granules of anhydrate of the compound of the formula I of modification II (formation B) were prepared.

A 5% strength suspension of the respective water-dispersible granules in CIPAC D water (Ca$^{++}$/Mg$^{++}$ (4:1) hardness of 342 ppm and pH of from 6.0 to 7.0 was then prepared. This suspension was then mixed with 1% of Solvesso 200 (mixture of aromatic hydrocarbons) as a typical solvent for solvent-containing liquid formulations (e.g. EC). The corresponding spray liquor was then stored over a certain period at a certain temperature. For assessing the quality, the solid residue on a 75 μm sieve was determined after the storage.

Result

| Formulation | Storage time | Storage temperature | Residue on 75 μm sieve |
|---|---|---|---|
| A | 24 hours | 20° C. | 13.0% w/w |
| A | 24 hours | 30° C. | 14.3% w/w |
| A | 7 days | 20° C. | 16.8% w/w |
| A | 7 days | 30° C. | 19.3% w/w |
| B | 24 hours | 20° C. | 0.1% w/w |
| B | 24 hours | 40° C. | Traces |
| B | 7 days | 20° C. | Traces |
| B | 7 days | 40° C. | 0.1% w/w |

We claim:

1. Monoclinic 2-chloro-N-(4'-chlorobiphenyl-2-yl)-nicotinamide melting at 147-148° C. and of the formula I

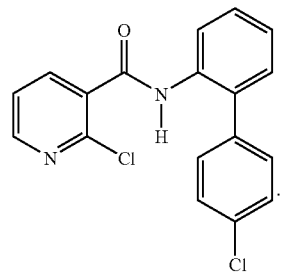

2. A process for the preparation of the compound I as claimed in claim 1, wherein
   a) 2-chloro-N-(4'-chlorobiphenyl-2-yl)-nicotinamide melting at 144-145° C. and of the formula I is dissolved in a protic polar solvent or an aromatic hydrocarbon, and
   b) crystallizes out of the solvent after cooling.

3. A process for the preparation of the compound I as claimed in claim 2, wherein the protic polar solvent used is an alcohol, glycol, ketone, ether, ester or amide or dimethyl sulfoxide or a mixture thereof.

4. A process for the preparation of the compound I as claimed in claim 3, wherein the protic polar solvent used is an alcohol, ester or ketone.

5. A process for the preparation of the compound I as claimed in claim 4, wherein the alcohol used is methanol or ethanol.

6. A process for the preparation of the compound I as claimed in claim 2, wherein the compound of the formula I is dissolved at from 20 to 150° C. in stage a).

7. A process for the preparation of the compound I as claimed in claim 2, wherein the compound of the formula I is dissolved at from 40 to 115° C. in stage a).

8. A fungicide containing the compound of the formula I as claimed in claim 1 and inert additives.

9. A fungicide as claimed in claim 8, which contains from 0.1 to 95% by weight of the compound of the formula I.

10. A method for controlling harmful fungi, wherein the harmful fungi, their habitat or the plants, area or materials or spaces to be kept free from them are treated with a fungicidal amount of monoclinic 2-chloro-N-4'-chlorobiphenyl-2-yl)-nicotinamide melting at 147-148° C. and of the formula I

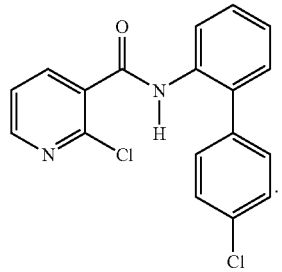

11. The method of claim 10, wherein the compound of formula I is present in the form of a composition further comprising inert additives.

* * * * *